(12) United States Patent
Imai et al.

(10) Patent No.: US 7,678,543 B2
(45) Date of Patent: Mar. 16, 2010

(54) METHOD FOR AMPLIFYING GENOMIC DNA

(75) Inventors: Takashi Imai, Chiba (JP); Mayumi Iwakawa, Chiba (JP); Yuichi Michikawa, Chiba (JP)

(73) Assignee: National Institute of Radiological Sciences, Anagawa (JP)

( * ) Notice: Subject to any disclaimer, the term of this patent is extended or adjusted under 35 U.S.C. 154(b) by 0 days.

(21) Appl. No.: 12/214,044

(22) Filed: Jun. 16, 2008

(65) Prior Publication Data

US 2009/0311753 A1     Dec. 17, 2009

(51) Int. Cl.
*C12Q 1/68* (2006.01)
*C12P 19/34* (2006.01)
*C07H 2/04* (2006.01)

(52) U.S. Cl. .................. 435/6; 435/91.2; 536/24.33

(58) Field of Classification Search ............. 435/6, 435/91.2; 536/22.1, 24.33
See application file for complete search history.

(56) References Cited

OTHER PUBLICATIONS

Langie, S.A.S. et al. Development and validation of a modified comet assay to phenotypically assess nucleotide excision repair. Mutagenesis, vol. 21, No. 2, pp. 153-158, 2006.*
Hosono, S. et al. Unbiased whole-genome amplification directly from clinical samples. Genome Res., vol. 13, pp. 954-964, 2003.*
Kwok et al., "Single-Molecule Analysis for Molecular Halotyping", Hum Mutat. 23(5), pp. 442-446, 2004.
Zhang et al, "Long-range polony halotyping of individual human chromosome molecules", Nature Genetics, vol. 38, pp. 382-387, 2006.
Iwakawa et al., "DNA repair capacity measured by high throughput alkaline comet assays in EBV-transformed cell lines and peripheral blood cells from cancer patients and healthy volunteers", Mutation Research 588, pp. 1-6, 2005.
Michikawa et al., "Reliable and Fast Allele-Specific Extensions of 3'-LNA Modified Oligonucleotides Covalently Immobilized on a Plastic Base, Combined with Biotin-dUTP Mediated Optical Detection", Analytical Sciences, vol. 22, pp. 1537-1545, 2006.
Buetow et al., "High-throughput development and characterization of a genomewide collection of gene-based single nucleotide polymorphism markers by chip-based matrix-assisted laser desorption/ionization time-of-flight mass spectometry", Proc. Natl. Acad Sci. U.S.A. vol. 98, No. 2, pp. 581-584, 2001.
Long et al., "An E-M Algorithm andTestingStrategy for Multiple-Locus Halotypes", Am. J. Hum. Genet. 56, pp. 799-810, 1995.
The International Hapmap Consortium, "A halotype map of the human genome", Nature, vol. 437, pp. 1299-1320, 2005.
Suga et al., "Halotyp-Based Analysis of Genes Associated With Risk of Adverse Skin Reactions After Radiotherapy in Breast Cancer Patients", Int. J. Radiation Oncology Biol. Phys, vol. 69, No. 3, pp. 685-693, 2007.
Konfortov et al., "An efficient metod for multi-locus molecular halotyuping", Nucleic Acids Research, vol. 35, No. 1, pp. 1-8, 2006.
Vishnevetsky et al., "Carotenoid sequestration in plants: the role of carotenoid-associated proteins", Trends in Plant Science vol. 4, Issue 6, Jun. 1, 1999, pp. 232-235.
Ruban et al., The Effects of Illumination on the Xanthophyll Composition of the Photosystem II Light-Harvesting Complexes of Spinach Thylakoid Membranes, Plant Physiol., vol 104, pp. 227-334, 1994.

* cited by examiner

*Primary Examiner*—Suryaprabha Chunduru
(74) *Attorney, Agent, or Firm*—Husch Blackwell Sanders Welsh & Katz

(57) ABSTRACT

A method for amplifying genomic DNA is provided. The method comprises the steps of: (1) incubating a cell-containing agarose solution at a pH of 9 to 12 and a temperature of 45 to 80° C. to produce a genomic DNA-dispersed agarose solution wherein 0.002 to 1 copies/5 microliter of single-stranded genomic DNA is dispersed; (2) solidifying the genomic DNA-dispersed agarose solution to produce a genomic DNA-dispersed agarose gel and neutralizing a pH of the gel; and (3) adding a DNA polymerase with strand displacement activity, primer and dNTP to the genomic DNA-dispersed agarose gel and incubating the gel at a temperature of 0 to 60° C. to amplify the genomic DNA.

11 Claims, 8 Drawing Sheets

METHOD FOR AMPLIFYING GENOMIC DNA

BACKGROUND OF THE INVENTION

1. Field of the Invention

The present invention relates to a method for amplifying genomic DNA.

2. Description of the Related Art

A haplotype (haploid genotype) consists of structurally continuous genetic markers on an individual chromosome. In genetic association studies, haplotypes facilitate more precise mapping of the target gene within a chromosomal region identified by an initial linkage analysis with conventional genetic markers such as single-nucleotide polymorphisms (SNPs) and microsatellites. Assessing the haplotype is also important for further functional studies, because genetic markers on the same chromosome molecule may functionally interact with each other.

Despite the importance of haplotypes, the difficulty of their experimental determination, owing to the presence of two almost identical copies of chromosomes in diploid cells, has prevented their general use. Haplotypes spanning a long distance (usually more than tens of kilobase pairs) or consisting of many genetic markers are difficult to experimentally assess. Currently, most haplotypes are indirectly reconstructed by (1) statistical estimation from conventional genotype data or (2) inference from family data. The reliability of statistical estimation depends on various factors such as the number of genetic markers, population size, allele frequencies and linkage disequilibrium between the genetic markers. Inference from family data can be limited by the availability of DNA samples.

Recently, an increasing number of molecular haplotyping techniques have been proposed (Kwok, P.-Y & Xiao, M "Single-molecule analysis for molecular haplotyping." Hum. Mut. 23, 442-446 (2004)). The polony approach (colony formation of target locus amplification products within a polyacrylamide gel by exogenously added Taq DNA polymerase, followed by in-gel sequential fluorescent single-base extension) has been successfully used for molecular haplotyping at the chromosome-wide level (Zhang, K. et al. "Long-range polony haplotyping of individual human chromosome molecules. Nat. Genet. 38, 382-387 (2006)).

BRIEF SUMMARY OF THE INVENTION

However, the polony approach has not yet entered general use, probably because of the difficulty of processing gel images for large numbers of loci. In the polony approach, immobilization of template DNA within a polyacrylamide gel matrix has the advantage of spatial separation of the DNAs from different chromosomes while maintaining their structural integrity; however, this immobilization becomes a limitation when the amplified materials are to be subjected to further analysis.

Under the situation, it has been required to develop a genomic DNA amplification method (1) that is not limited by the distance spanned by the haplotype or by the number of genetic markers and (2) wherein the amplified DNA could be selectively recovered after amplification in the gel.

The present inventors has intensively studied for the above genomic DNA amplification method. As a result, the present inventors found the following findings:

(1) DNA immobilized within agarose gel, instead of polyacrylamide gel, could serve as a template for enzymatic amplification. In the agarose gel, random oligonucleotide primer-mediated multiple displacement amplification was performed by exogenously added DNA polymerase with strand displacement activity. Since this reaction does not require a temperature so high as to melt the gel, the integrity of the gel can be maintained throughout the reaction. The immobilized DNA is fixed in the agarose gel. On the other hand, the DNA polymerase can easily access to the immobilized DNA to conduct an amplification reaction in the agarose gel. Accordingly, extremely small amount of DNA can be certainly amplified.

(2) The amplified products can then be easily recovered in solution by simple heating of the gel, making them available for use as templates for further analysis such as conventional PCR.

The present invention has been accomplished based on the above findings. Accordingly, the present invention relates to a method for amplifying genomic DNA comprising the steps of (1) incubating a cell-containing agarose solution at a pH of 9 to 12 and a temperature of 45 to 80° C. to produce a genomic DNA-dispersed agarose solution wherein 0.002 to 1 copies 15 microliter of single-stranded genomic DNA is dispersed;

(2) solidifying the genomic DNA-dispersed agarose solution to produce a genomic DNA-dispersed agarose gel and neutralizing a pH of the gel; and (3) adding a DNA polymerase with strand displacement activity, primer and dNTP to the genomic DNA-dispersed agarose gel and incubating the gel at a temperature of 0 to 60° C. to amplify the genomic DNA.

DETAILED DESCRIPTION OF THE INVENTION

Figure 1:
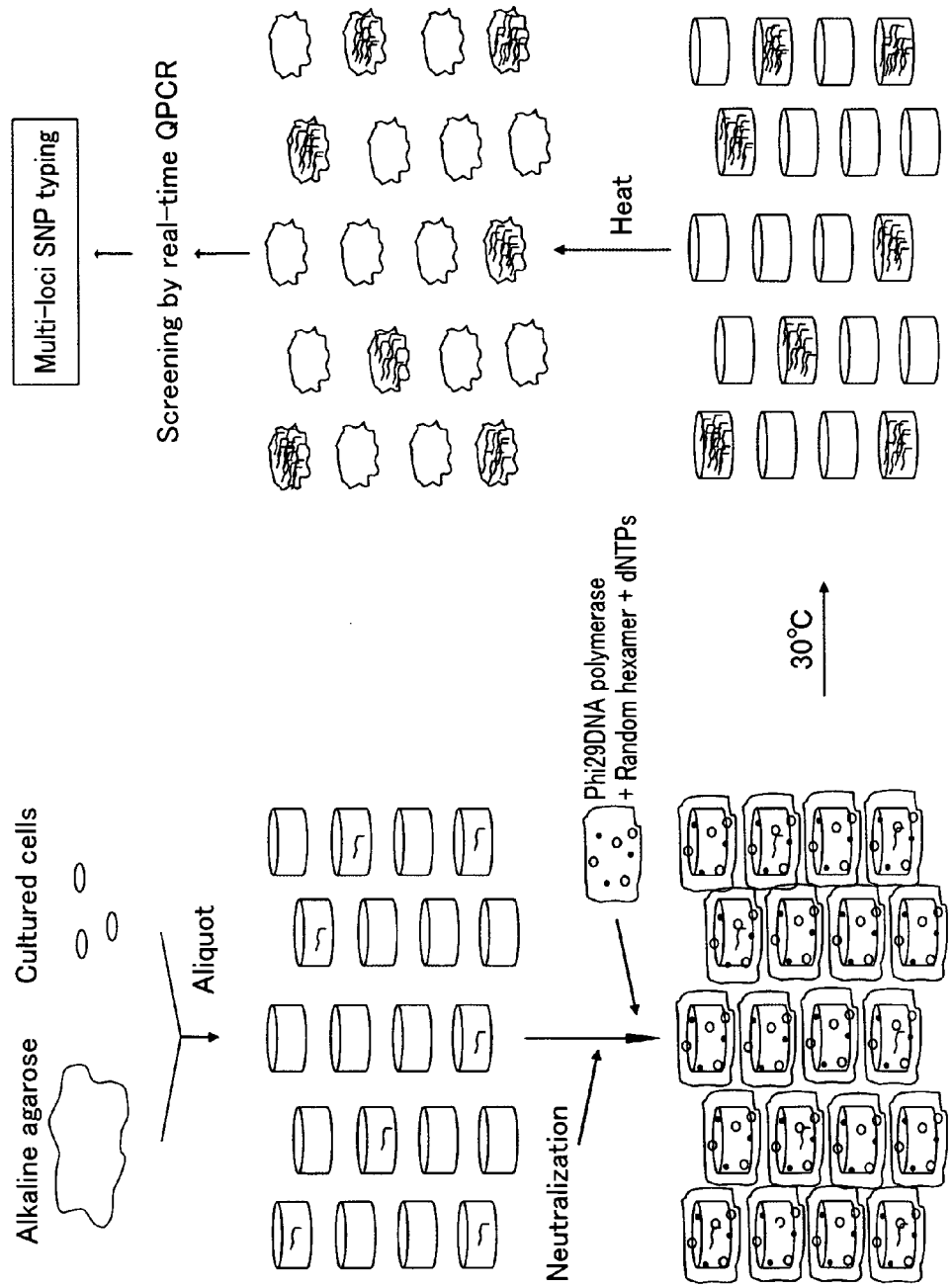
FIG. 1: Outline of molecular haplotyping experiments. Intact cultured cells were mixed with heated alkaline agarose gel solution and then divided into multiple small-volume gel pieces. The gel pieces were allowed to cool until they solidified and were then neutralized. A reaction mixture containing Phi29 DNA polymerase, random hexamers, and dNTPs was added to each gel, and then the gels were incubated at 30° C. for 16 h. They were then heated to terminate the reaction and solubilized. Gels with the target chromosome were screened by real-time QPCR and subjected to multi-locus genotyping.

A method for amplifying genomic DNA of the present invention comprises the steps of:
(1) incubating a cell-containing agarose solution at a pH of 9 to 12 and a temperature of 45 to 80° C. to produce a genomic DNA-dispersed agarose solution wherein 0.002 to 1 copies/5 microliter of single-stranded genomic DNA is dispersed;
(2) solidifying the genomic DNA-dispersed agarose solution to produce a genomic DNA-dispersed agarose gel and neutralizing a pH of the gel; and
(3) adding a DNA polymerase with strand displacement activity, primer and dNTP to the genomic DNA-dispersed agarose gel and incubating the gel at a temperature of 0 to 60° C. to amplify the genomic DNA.

Step (1)

Cell to be used in the present invention is not limited to particular one. Accordingly, the present invention can apply to a cell from haploid organism and a cell from diploid organism. The present invention is particularly suitable for amplifying a genomic DNA of the cell from diploid organism. Examples of the diploid organism include human, mouse, yeast, etc. The present invention is particularly suitable for amplifying human genomic DNA.

Genomic DNA refers to DNA which exists in an individual cell. Examples of the genomic DNA include nuclear DNA, mitochondrial DNA, chloroplast DNA, etc. The present invention is particularly suitable for amplifying the nuclear DNA.

Agarose generally used in the field of the molecular biology can be used for the present invention without particular limitation. Agarose which has a melting point of 80 to 100° C. and provides a high-strength gel (gel strength: >1000 g/cm$^2$), is preferable.

Solvent for dissolving the agarose includes water, etc. In order to easily adjust pH of a cell-containing agarose solution, a solvent having no pH buffering ability such as water is preferable.

The cell-containing agarose solution may contain a pH adjuster such as NaOH, KOH, etc. Furthermore, the cell-containing agarose solution may contain an ion-strength adjuster such as NaOH in order to stabilize a single-stranded genomic DNA in an agarose solution. The cell-containing agarose solution can be prepared by adding a cell to an agarose solution.

Incubation is carried out at a pH of 9 to 12, preferably 10 to 11 and particularly preferably 11. Furthermore, the incubation is carried out at a temperature of 45 to 80° C., preferably 50 to 70° C. and particularly preferably 60° C. When the incubation is carried out a pH of 9 to 12 and a temperature of 45 to 80° C., a cell can be dissolved and its genomic DNA, which is denatured to a single strand, can be dispersed in an agarose solution. Furthermore, when the incubation is carried out a pH of 9 to 12, an aggregation of the single-stranded genomic DNA in the agarose solution can be avoided.

Incubation time is not particularly limited so long as a single-stranded genomic DNA-dispersed agarose solution can be obtained. For example, the incubation time can be 5 to 300 min, preferably 15 to 60 min and particularly preferably 30 min.

By the incubation, a cell is lysed and its genomic DNA, which is denatured to a single strand, is dispersed into an agarose solution.

During the incubation, an agarose solution is preferably agitated so that a single-stranded genomic DNA is uniformly dispersed into the agarose solution. A gentle agitation which does not disrupt the genomic DNA (for example, an agitation rate of 50 min$^{-1}$) is preferable. Examples of an agitation means include the inversion of an agarose solution-containing vessel, the shaking the vessel, etc.

After the incubation, an agarose solution contains a single-stranded genomic DNA at a concentration of 0.002 to 1 copies/5 microliter, preferably 0.02 to 0.5 copies/5 microliter and particularly preferably 0.2 to 0.4 copies/5 microliter. When the agarose solution contains the single-stranded genomic DNA at a concentration of 0.002 to 1 copies/5 microliter, an agarose gel wherein the single-stranded genomic DNA is uniformly dispersed (in other words, an agarose gel having no tangled-homologous chromosomes) can be obtained in the following step (2).

The copy number of the single-stranded genomic DNA in the agarose solution after the incubation can be controlled by the number of cells to be added to the agarose solution prior to the incubation. For example, when an agarose solution containing a diploid cell at a concentration of 0.05 cells/5 microliter is subjected to incubation, the copy number of the single-stranded genomic DNA in the agarose solution after the incubation is 0.2 copies/5 microliter (0.05 cells×two homologous chromosomes×two single-stranded genomic DNA).

Prior to the step (2), the agarose solution obtained in the step (1) is preferably divided to plural aliquots so that amplified genomic DNA obtained in the step (3) can be easily recovered. The number of aliquots is that each of aliquots contains one kind of the single-stranded genomic DNA, for example 96.

Step (2)

Solidification temperature is not particularly limited so long as the genomic DNA-dispersed agarose solution obtained in the step (1) can be solidified to a gel. For example, the solidification temperature can be 0 to 30° C., preferably 0 to 20° C. and particularly preferably 0 to 10° C.

Solidification time is not particularly limited so long as the genomic DNA-dispersed agarose solution obtained in the step (1) can be solidified to a gel.

Next, a pH of the solidified agarose gel is neutralized. Neutralization of the pH of the gel can avoid an alkaline inactivation of a polymerase with strand displacement activity to be used in the following step (3). A pH of the gel after the neutralization is not particularly limited so long as the inactivation of the polymerase can be avoided. For example, the pH of the gel after the neutralization is a pH of 6.5 to 8.5, preferably a pH of 7.0 to 8.0 and particularly preferably a pH of 7.5.

Step (3)

DNA polymerase to be used in the present invention is a polymerase with strand displacement activity. The DNA polymerase has an optimum temperature of less than the melting point of the agarose gel obtained in the step (2). Specifically, the DNA polymerase has an optimum temperature of 0 to 60° C., preferably 0 to 40° C. and particularly preferably 30° C.

The DNA polymerase having such optimum temperature does not require a primer-annealing step at a high temperature of 90° C. or more. Accordingly, no thermal melting of the agarose gel occurs in the step (3). When a DNA polymerase with strand displacement activity and an optimum temperature of 0 to 60° C. is used, genomic DNA can be amplified while being fixed in the agarose gel.

Examples of the DNA polymerase include Phi29 DNA polymerase, Bst DNA polymerase, etc. Phi29 DNA polymerase is particularly preferable. Phi29 DNA polymerase is a DNA polymerase with strand displacement activity and an optimum temperature of 30° C.

A single DNA polymerase or a combination of two or more DNA polymerases can be used for the present invention. A DNA polymerase with strand displacement activity is a known substance and can be readily acquired commercially, or it can be easily prepared.

Primer refers to a DNA fragment which complements to a template DNA (i.e., a single-stranded genomic DNA to be amplified) and provides a DNA polymerase having the strand displacement activity with free 3'OH group (3'OH group is required to conduct the strand extension by the DNA polymerase).

In order to attain a high-coverage amplification of a genomic DNA, the primer has preferably random sequence. Length of the primer varies depending on the coverage of whole genome sequences. When Phi29 DNA polymerase is used, the length of the primer is preferably 6 bases. A person skilled in the art could have easily designed the primer having the random sequence for a target DNA to be amplified.

When Phi29 DNA polymerase is used, a primer is preferably modified with phosphorothioate in order to protect the primer from 3'-exonuclease activity of Phi29 DNA polymerase.

When Phi29 DNA polymerase is used, the primer preferably consists of the following sequence: $N_1N_2N_3N_4N_5N_6$ ($N_1, N_2, N_3, N_4, N_5$ and $N_6$ each may be identical or different, which are bases randomly selected from the group consisting of A, C, G, and T. $N_5$ and $N_6$ are modified with phosphorothioate to prevent degradation of primers by the 3'-5' exonuclease activity of Phi29DNA polymerase).

Deoxynucleoside triphosphate (dNTP) is used as a raw material of a new strand when a DNA polymerase with strand displacement activity synthesizes the new strand. Examples of dNTP include dATP, dCTP, dGTP and dTTP dNTP is a known substance and can be readily acquired commercially, or it can be easily prepared.

Each additive amount of a DNA polymerase with strand displacement activity, a primer and dNTP is not particularly limited so long as a sufficient amplification reaction can be attained. A person skilled in the art could easily determine each additive amount of them in view of an incubation condition used in the step (3).

In the step (3), a DNA polymerase buffer which improves the amplification efficacy, Tween-20 which promotes easy access of a DNA polymerase to an agarose gel, and/or bovine serum albumin which stabilizes the DNA polymerase may be used.

Incubation is carried out at a temperature which is less than the melting point of the agarose gel obtained in the step (2) and wherein a DNA polymerase can function. Specifically, the incubation is carried out at a temperature of 0 to 60° C., preferably 0 to 40° C. and particularly preferably 30° C. When the incubation is carried out at a temperature of 0 to 60° C., a genomic DNA can be amplified while being fixed in the agarose gel.

Incubation time is not particularly limited so long as an intended DNA amplification can be obtained. For example, the incubation time can be 2 to 24 hour, preferably 9 to 20 hour and particularly preferably 16 hour.

When an amplification reaction is carried out by using different kinds of DNA polymerases, a DNA polymerase and primer may be selectively removed from an agarose gel after the first amplification reaction and then another DNA polymerase and primer may be added to the gel to conduct the second amplification reaction.

In the step (3), a single-stranded genomic DNA is amplified while being fixed in an agarose gel. Accordingly, an agarose gel fraction containing an amplified genomic DNA of interest can be easily obtained. When an agarose solution obtained in the step (1) is divided to plural aliquots wherein each of aliquots contains one kind of the single-stranded genomic DNA, an agarose gel fraction containing an amplified genomic DNA of interest can be more easily obtained.

Amplified genomic DNA can be easily recovered by heat-melting an agarose gel containing the amplified genomic DNA. Recovered genomic DNA can be easily subjected to a PCR reaction for further analysis.

As substantiated in EXAMPLE below, the present invention can amplify a genomic DNA without causing the fragmentation of the genomic DNA. Furthermore, the present invention can amplify a genomic DNA in a manner that each strands of the genomic DNA are spatially separated from each other in an agarose gel. Furthermore, an amplification product obtained in an agarose gel can be easily and selectively recovered for further analysis such as haplotype analysis. Accordingly, the present invention can advantageously provide a DNA sample to be subjected to a genetic analysis, especially, an analysis of haplotype consisting of genetic markers widely distributed in an individual chromosome.

EXAMPLE

Next, the effect of the present invention will be specifically explained with reference to EXAMPLE. However, the present invention is not intended to be limited to it.

In EXAMPLE, an amplification of a genomic DNA was carried out for Epstein Barr Virus (EBV)-transformed human lymphoblastoid cell lines.

Steps (1) to (3)

EBV-transformed human lymphoblastoid cell lines were established from peripheral blood of the healthy volunteers in accordance with the publication (Iwakawa, M. et al. DNA repair capacity measured by high throughput alkaline comet assays in EBV-transformed cell lines and peripheral blood cells from cancer patients and healthy volunteers. Mutat. Res. 588, 1-6 (2005)). These cell lines were grown in RPMI-1640 medium with 20% fetal bovine serum. They were washed once with phosphate-buffered saline (PBS), and the number of cells was counted. The concentration was adjusted to 50000 cells/ml of PBS, and then 10-ml aliquots (50 cells) were transferred to new 0.5-microliters Eppendorf tubes, which were stored at −80° C. until use.

Type I agarose (Sigma-Aldrich, St. Louis, Mo., USA; melting point: 87° C.; gel strength: 1200 g/cm$^2$) weighing 3.75 g was suspended in 100 ml sdH$_2$O (sterile distilled water), thoroughly heated by microwave, and then allowed to gradually cool down to 60° C. on a heat block. Then, 960 ml of the agarose solution was mixed with 240 ml of prewarmed alkaline solution (0.5 N NaOH and 1.5 M NaCl) to make an alkaline agarose solution (pH=11) (agarose concentration: 3 wt %), which was maintained at 60° C.

Frozen human lymphoblastoid cell lines were thawed at room temperature. Cell suspensions containing 10 cells were gently added to the 1 ml of 3% alkaline agarose solution to give a cell-containing agarose solution (pH=11). The cell-containing agarose solution was incubated at 60° C. for 30 min, with occasional gentle inversions. After incubation, the cell-containing agarose solution contained 0.2-0.4 copies of single-stranded chromosomes/5 microliter.

Next, 5-microliters aliquots (number of aliquots: 93) containing 0.2-0.4 copies of single-stranded chromosomes (0.05-0.10 cells) were transferred to new 1.2-ml microtubes (AB-gene, Surrey, UK), left at room temperature (24° C.) for 5 min, and then cooled (0° C.) on ice for 5 min to be solidified.

Additionally, two 5-microliters gels containing 100 times as many cells (5 cells; 20 copies of single-stranded chromosomes) and one 5-microliters empty gel were prepared as positive and negative controls, respectively.

A solution containing a polymerase with strand displacement activity, primer and dNTP was prepared (hereinafter referred to as "igMDA solution"). The igMDA solution contained 0.75 units/microliters Phi29 DNA polymerase (optimum temperature: 30° C.) (New England Biolab), 1×Phi29 DNA polymerase buffer, 50 micromolars (μM) random hexamers with phosphorothioate modification on two consecutive nucleotides at the 3'-end, 1.25 mM dNTPs, 1% Tween-20, and 0.1 mg/ml Bovine Serum Albumin.

The random hexamers used (primer) consisted of the following sequence: $N_1N_2N_3N_4N_5N_6$ ($N_1$, $N_2$, $N_3$, $N_4$, $N_5$ and $N_6$ each may be identical or different, which are bases randomly selected from the group consisting of A, C, G, and T. $N_5$ and $N_6$ are modified with phosphorothioate.)

Solidified aliquots of gel were washed at room temperature for 10 min with a neutral solution (0.5 M Tris/HCl, pH 7.4, and 3 M NaCl) and by 0.5×SSC (75 mM NaCl and 7.5 mM sodium citrate, pH 7.0) for at least 10 min. The pH of the neutralized gel was 7.5. Two volumes of the igMDA solution were added to each gel, which was incubated at 30° C. for 16 h with constant gentle shaking. The gels were stained with SYBR Green I as described in the following section or added to a 100× volume of sdH$_2$O and heated at 100° C. for 10 min to terminate the reaction and solubilize the gel.

The steps (1) to (3) above are summarized in FIG. 1.

TEST EXAMPLE

Analytical procedures used in TEST EXAMPLE are described below.

SYBR Green I Staining of the Gel and Image Capture

The gels were stained with 100×SYBR Green I (Cambrex Bioscience, Rockland, Me.) in TE (10 mM Tris, pH 7.4, and 1 mM EDTA) at room temperature for 30 min. The gels were destained twice by TE for 30 min and placed on a UV transmitter (wavelength 365 nm). Gel images were captured by a digital camera with UV filter.

Real-Time Quantitative PCR (Real-Time QPCR)

Ten microliters of reaction mixture contained 0.5 units HotStar Taq DNA polymerase, 1× HotStar Taq DNA polymerase buffer, 0.2 mM dNTPs, 3.3×SYBR Green I, 0.2 micromolars of each PCR primer, and 4 microliters template DNA (i.e., dissolved solution of the amplified genomic DNA-containing agarose gel obtained in EXAMPLE). The mixtures were heated at 95° C. for 15 min and then subjected to 50 cycles of two-step temperature cycling (95° C. for 10 s and 65° C. for 40 s), followed by melting curve analysis from 65° C. to 95° C. with a ramp rate of 4.8° C./s in a LightCycler 480 thermal cycler (Roche Diagnostics, Basel, Switzerland). The crossing point (CP) of each amplification curve was determined by the maximum second derivative method.

On-Plastic Chip Allele-Specific Primer Extension (OPEXT)

Multiple SNP genotyping of the amplified genome DNA was performed by OPEXT as described previously in the publication (Michikawa, Y. et al. Reliable and fast allele-specific extension of 3'-LNA modified oligonucleotides covalently immobilized on a plastic base, combined with biotin-dUTP mediated optical detection. Anal. Sci. 22, 1537-1545 (2006)).

MassARRAY SNP Typing and Haplotype Estimation

MassARRAY SNP typing of the seven SNPs in the ATM region was carried out with genomic DNA extracted from 100 healthy volunteers in accordance with the manufacturer's instructions (Buetow, K. H. et al. High-throughput development and characterization of a genomewide collection of gene-based single nucleotide polymorphism markers by chip-based matrix-assisted laser desorption/ionization time-of-flight mass spectrometry. Proc. Natl. Acad. Sci. U.S.A. 98, 581-584 (2001)). Haplotypes of the seven SNPs were estimated by the Expectation Maximization algorithm (Long, J. C., Williams, R. C. & Urbanek, M. An E-M algorithm and testing strategy for multiple-locus haplotypes. Am. J. Hum. Genet. 56, 799-810 (1995)).

Hereinafter, a haplotype analysis conducted for the amplified genomic DNA obtained in EXAMPLE is explained.

First Screening of Target Locus Amplicons

A total of 96 gels prepared in EXAMPLE were screened for ATM locus on chromosome 11 by real-time QPCR with heat-solubilized gel portions as templates. PCR primers used in the screening are shown in Table 1.

Figure 2:
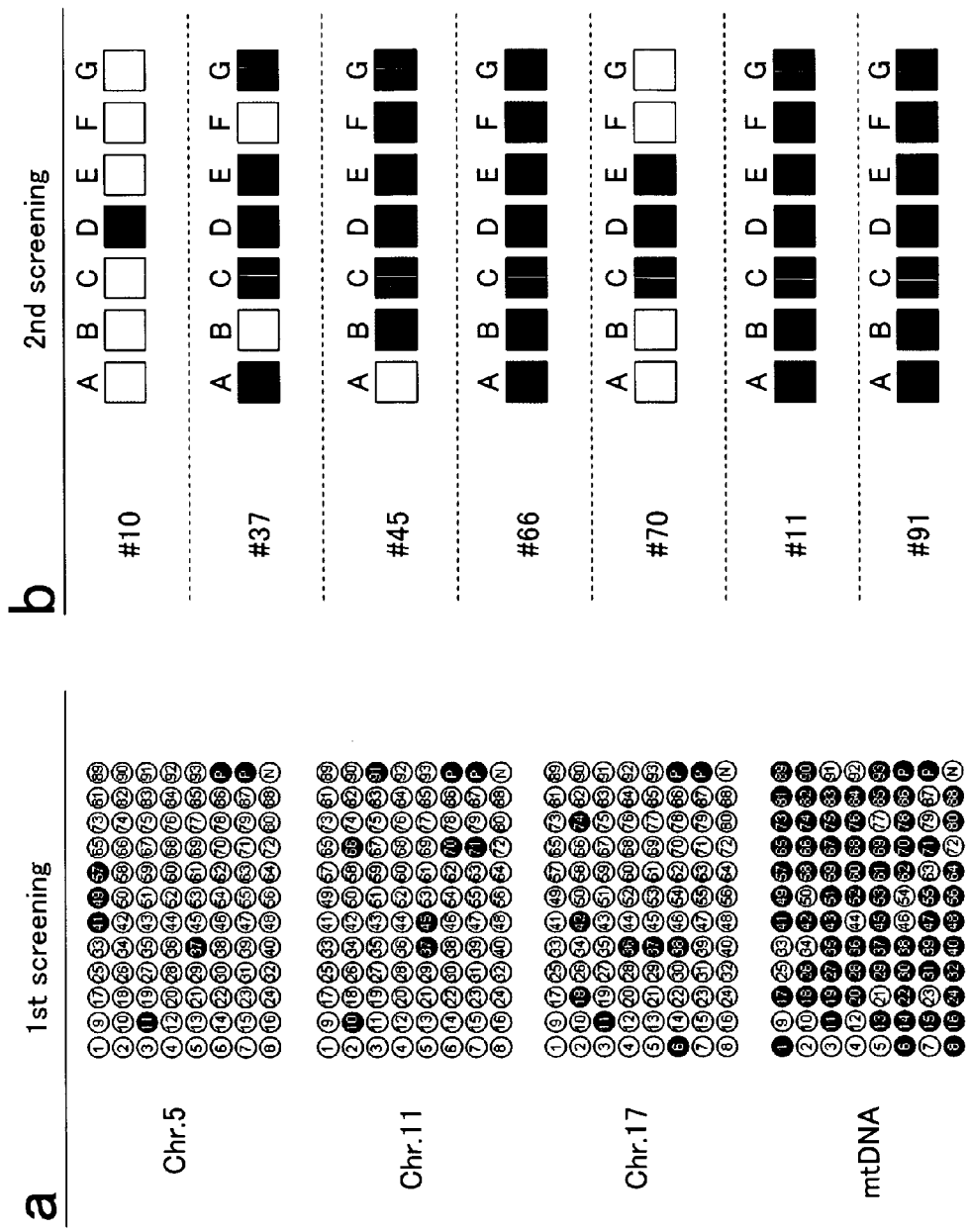
FIG. 2: Screening of target locus amplicons. (a) Results of first screening. Gels are serially numbered. A black circle with white lettering indicates a positive gel and a white circle with black lettering indicates a negative gel. P, positive control gel; N, negative control gel. (b) Results of second screening. Gels positive for chromosome 11 primer sets were further screened for those positive for the entire ATM region. A black square indicates a positive locus, and a white square indicates a negative locus. A, rs2280332; B, rs228589; C, rs1800054; D, rs664677; E, rs1800057; F, rs1801516; Q rs227055.

Among them, nine gels, including the two positive control gels, were positive for the locus (FIG. 2a). As controls, the gels were screened for other loci (Securin locus on chromosome 5, DNA ligase III locus on chromosome 17, and mitochondrial DNA). The number of gels positive for each locus was 7, 10, and 71, respectively, including the two positive control gels. All three nuclear chromosome loci appeared at similar frequency, and they seemed to be well dispersed (In other words, no aggregation of DNA occurred in the gels), with only one exceptional gel (#37) having all loci together. The high number of mitochondrial DNA-positive gels most likely reflected the higher copy number relative to that of nuclear chromosomes within a cell.

Second Screening for Entire ATM Locus Amplicons

The nine gels with the ATM locus amplicon, including the two positive controls, were further screened for those possessing the entire ATM locus. Six additional loci spanning 240 kb of this region was selected for this purpose (Table 1). PCR primers used in the screening are shown in Table 1.

Five gels, including the two positive controls, were positive for all six loci (FIG. 2b). This result substantiates that the present invention provides a genomic DNA which can be subjected to an analysis of haplotype spanning in a long region of 240 kb. The generally demanded haplotype size, which is the normal range of linkage disequilibrium across the human genome, is 50 to 100 kb (International HapMap Consortium. A haplotype map of the human genome. Nature 437, 1299-1320 (2005)). Thus, the capability of the present invention to selectively amplify a single-stranded genome DNA of 240-kb, as demonstrated in this EXAMPLE, assures its usefulness.

The amplicons in the gel were recovered in solution in PCR-ready form. Accordingly, increasing the number of genetic markers for precise construction of haplotypes was not a technical challenge.

The rest of the gels contained only part of the region and were excluded from further analysis. In particular, gel #37, which had all three chromosome loci, showed discontinuity of positive areas, indicating an irregular amplification reaction within this gel, presumably due to aggregation of template chromosome DNA.

Multi-Locus Genotyping of the Entire ATM Locus Amplicons

Figure 3:
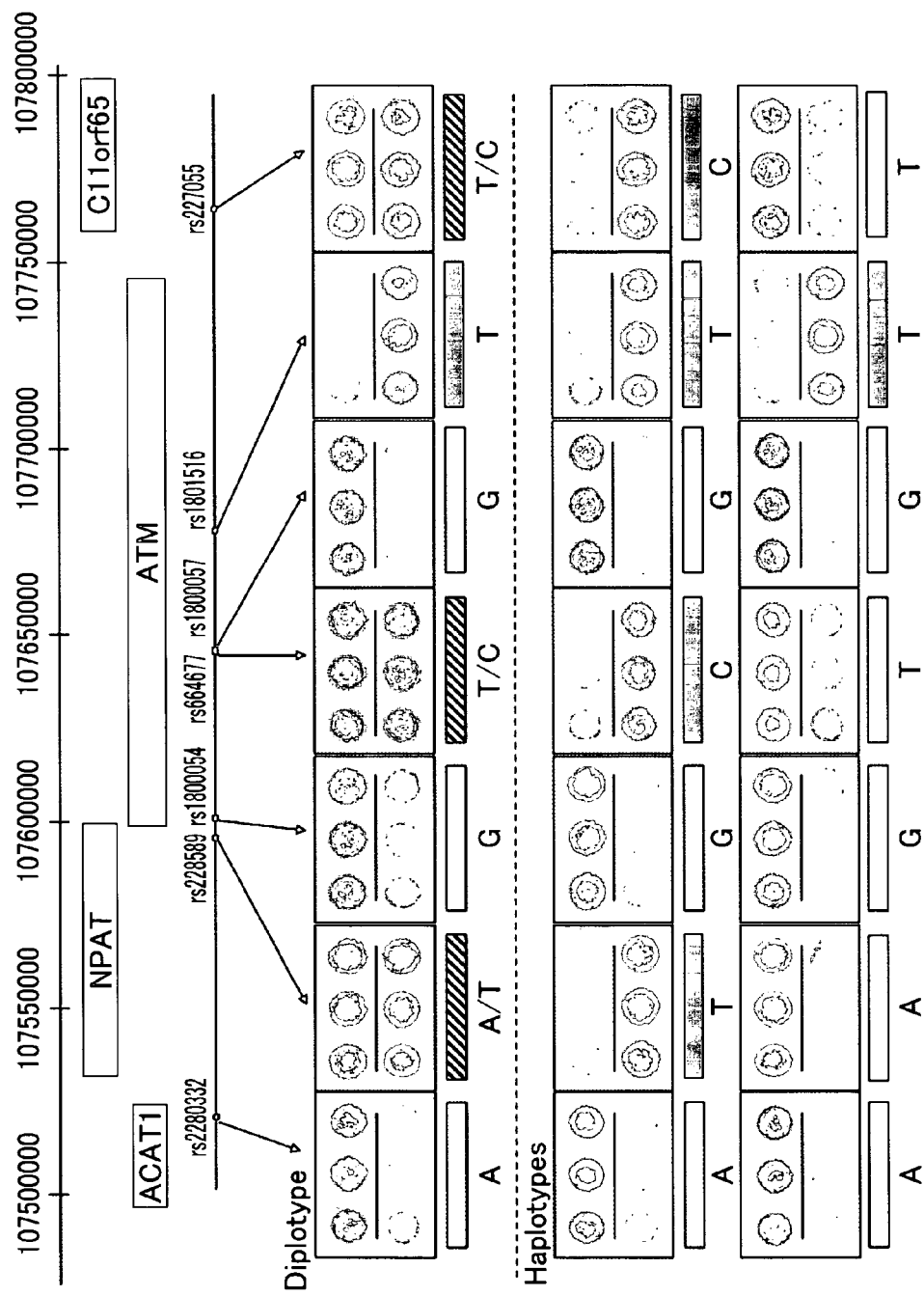
FIG. 3: Haplotype determination of the human ATM region. Seven SNPs spanning 240 kb of the human ATM region on chromosome 11 were analyzed for the amplified materials. Allele-specific oligonucleotide primers were spotted in triplicate, with allele 1 above and allele 2 below. Spot images of the original diplotype and derived haplotypes are shown. White bars under spot images indicate homozygosity for allele 1. Black bars indicate homozygosity for allele 2. Hatched bars indicate heterozygous alleles.

The five gels with the entire ATM locus amplicon were processed by genotyping seven SNPs, respectively located within the seven loci used in the screening. Three heterozygous SNPs were detected in both positive control gels (FIG. 3; diplotype). All seven SNP genotypes of the two positive control gels were identical to those of genomic DNA extracted from an aliquot of a blood sample from the same individual (data not shown). None of the SNPs showed heterozygosity in the other three gels, proving successful isolation of homologous chromosomes within these gels. Two gels (#66 and #91) showed identical haplotypes (FIG. 3; upper haplotype) and the third gel (#71) showed the complementary haplotype (FIG. 3; lower haplotype). These observations further confirmed the effectiveness of the present invention.

Figure 4:
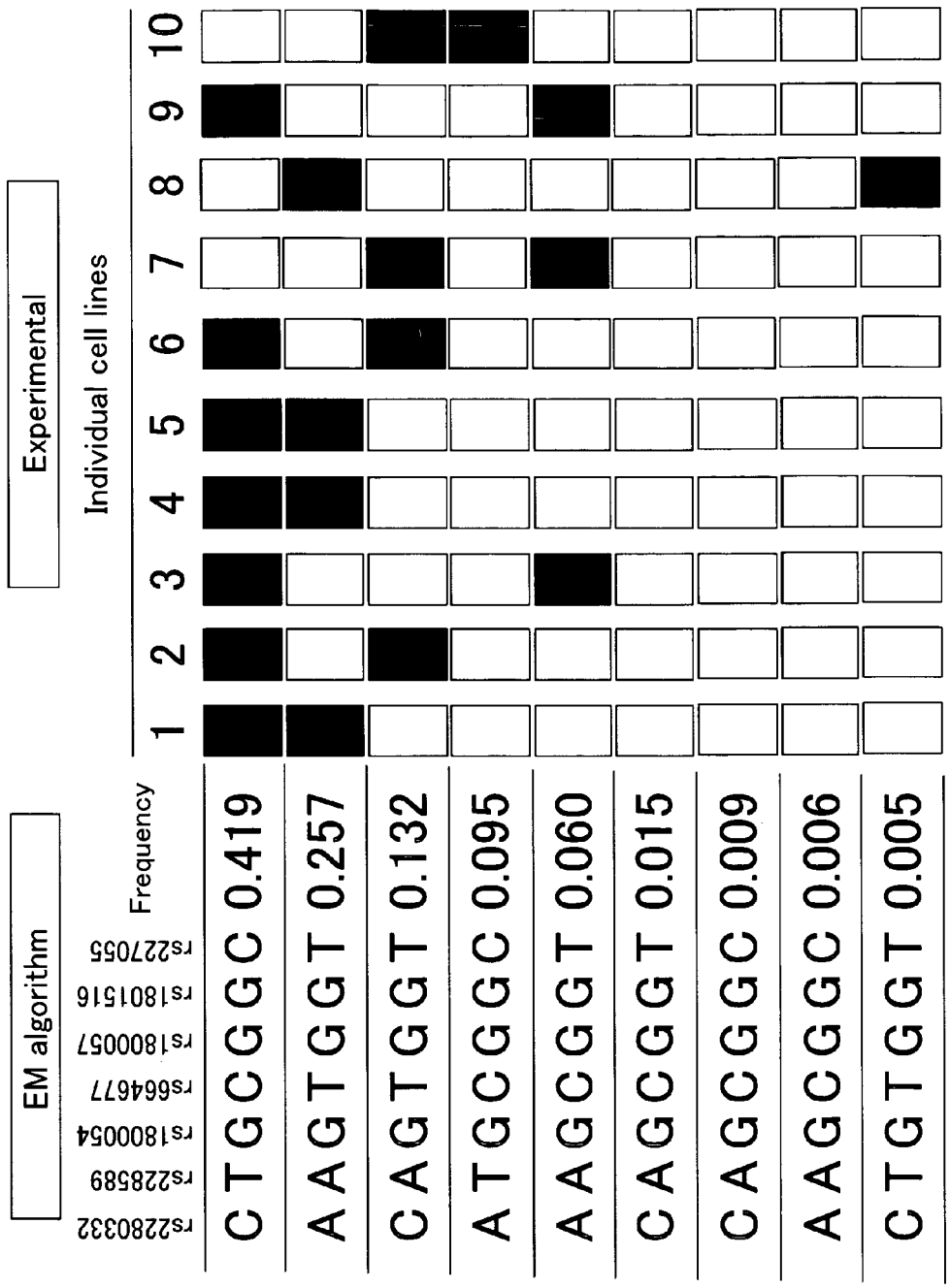
FIG. 4: Summary of ATM haplotypes determined in 10 EBV-transformed B lymphoblastoid cell lines. Haplotypes of seven SNPs in 100 healthy volunteers were statistically estimated and numbered in order of their frequency ("EM algorithm"). Haplotypes of individual cell lines determined experimentally are plotted to the right of the estimated haplotype patterns ("Experimental"). Black square indicates that the cell line had the estimated haplotype as shown in the left column. White square indicates that the cell line had not the estimated haplotype as shown in the left column.

Next, the present invention was used to analyze 10 EBV-transformed human lymphoblastoid cell lines in the same manner as explained above. The average number of gels positive for chromosome 11 in the first screening was 18.7 (Table 2). Among the gels positive in the first screening, 38.2% on average contained amplicons of the entire ATM locus. Genotyping results are summarized in FIG. 4. All of the experimentally determined haplotype patterns were found in the list of haplotypes estimated statistically from SNP data on 100 healthy volunteers, assuring the reliability of the present invention. Accordingly, the present invention provides a genomic DNA which can be subjected to an experimental analysis of haplotype.

REFERENCE EXAMPLE

REFERENCE EXAMPLE is provided to substantiate that human genomic DNA is indeed amplified in an agarose gel.

Human genomic DNA was individually extracted from blood donated by 100 healthy volunteers for a previous study (Suga, T. et al. Haplotype-based analysis of genes associated with risk of adverse skin reactions after radiotherapy in breast cancer patients. Int. J. Radiat. Oncol. Biol. Phys. 69, 685-693, 2007). All of the donors gave written informed consent to participate in this study, which was approved by the Ethical Committee at the National Institute of Radiological Sciences.

Nine hundred and sixty (960) ml of the agarose solution, which was prepared in the same manner with EXAMPLE, was mixed with 240 ml of prewarmed alkaline solution (0.5 N NaOH and 1.5 M NaCl) to make a 3% alkaline agarose solution, which was maintained at 60° C. The 3% agarose solution was mixed with 1 ng of human genomic DNA and incubated at 60° C. for 30 min with occasional gentle inversions. Next, 20-microliters aliquots were transferred to new 1.5 ml Eppendorf tubes, left at room temperature for 5 min, and then cooled on ice for 5 min.

Figure 5:
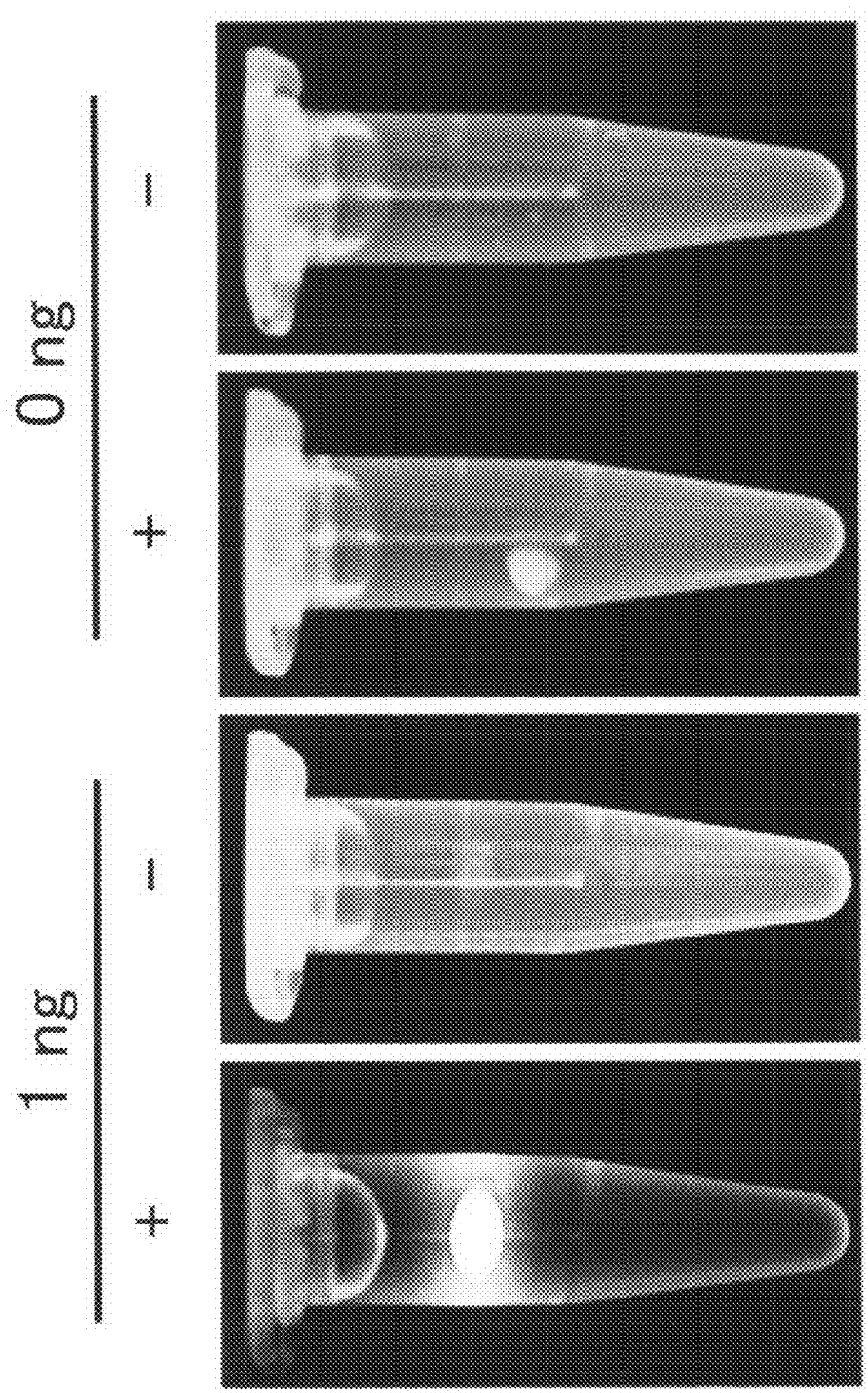
FIG. 5: SYBR Green I staining of agarose gels. Agarose gels with 1 ng or 0 ng of human genomic DNA were incubated with (+) or without (−) Phi29 DNA polymerase for 16 h. Gels were stained with SYBR Green I for 30 min and destained for 1 h before images were obtained.
Figure 6:
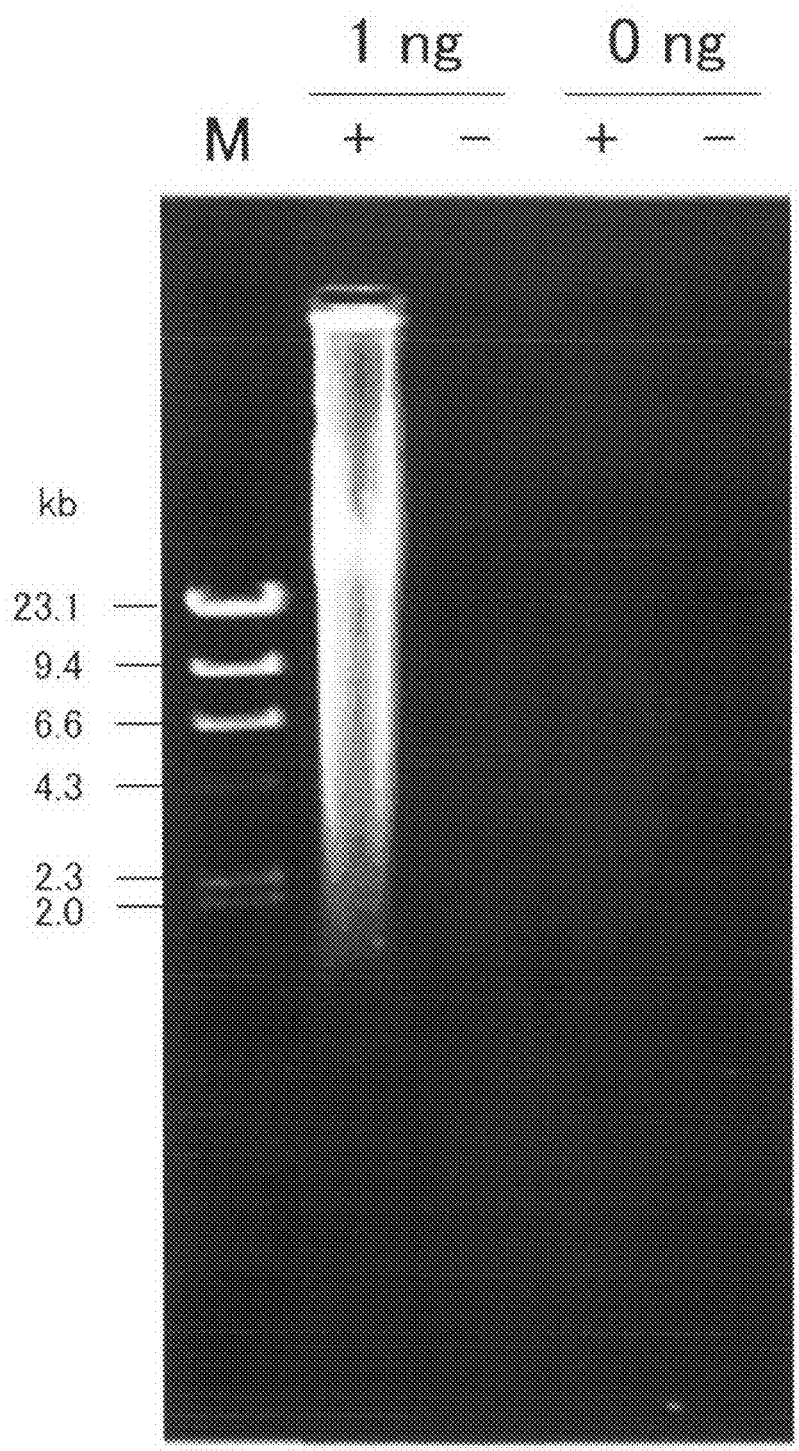
FIG. 6: Agarose gel electrophoresis of heat-solubilized agarose gel. Agarose gels with 1 ng or 0 ng of human genomic DNA were incubated with (+) or without (−) Phi29 DNA polymerase for 16 h. Agarose gel stained with SYBR Green I as in FIG. 5 was then added to sdH$_2$O to make a 5× dilution and heat solubilized. Four-microliter fractions of solubilized agarose were applied to 0.6% agarose gel for electrophoresis. The gel was stained after electrophoresis with SYBR Green I for 30 min and then destained for 1 h before an image was obtained.

The agarose gel containing 1 ng of human genomic DNA was incubated for 16 h with exogenously added Phi29 DNA polymerase and random hexamer oligonucleotides. The Phi29 DNA polymerase and random hexamer oligonucleotides were those used in EXAMPLE. The gel became strongly fluorescent with SYBR Green I staining (1 ng+), whereas the same gel incubated in the absence of the enzyme did not show such fluorescence (1 ng−), indicating that the fluorescence resulted from enzymatic activity of the Phi29 DNA polymerase (FIG. 5). Phi29 DNA polymerase and random hexamer oligonucleotides alone were not enough to cause such fluorescence in an empty agarose gel (0 ng+). Thus, it was concluded that the observed strong SYBR Green I fluorescence of the gel was a result of input DNA-oriented enzymatic amplification of genomic materials by exogenously added Phi29 DNA polymerase. The genomic amplification was further confirmed by electrophoresis of the heat-solubilized agarose gels (FIG. 6).

Template DNA Replication within Agarose Gel

Real-time quantitative PCR was used to assess quantitative changes to input DNA at various chromosome loci after the genomic amplification reaction within the agarose gel. Three nuclear chromosome loci (Securin gene locus on chromosome 5, ATM gene locus on chromosome 11, and DNA ligase III gene locus on chromosome 17) and one mitochondrial DNA locus were selected for this purpose. Procedures of RT-QPCR and primers used are the same as those in EXAMPLE.

Figure 7:
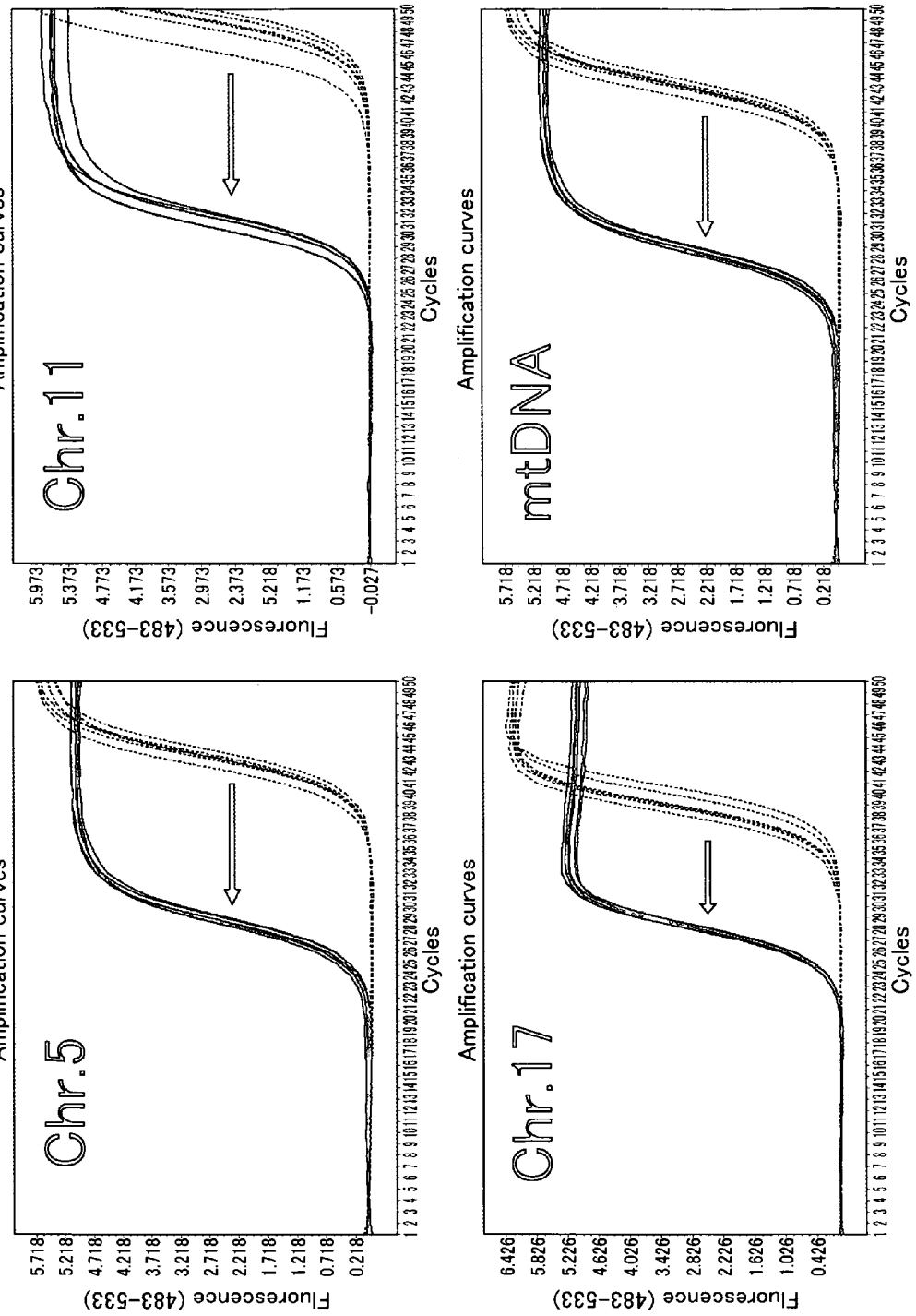
FIG. 7: Real-time quantitative PCR (QPCR) of heat-solubilized agarose gel. Agarose gels with 1 ng of human genomic DNA were incubated with or without Phi29 DNA polymerase for 16 h. After incubation, the gels were added to sdH$_2$O to make a 100× dilution and then heat solubilized. Four-microliter fractions of solubilized agarose were used as templates for real-time quantitative PCR. Gels were prepared in duplicate. Real-time QPCR was performed in triplicate for each gel. Solid line, with Phi29 DNA polymerase; broken line, without Phi29 DNA polymerase. PCR primers used for each locus are listed in Table 1.

All four loci were dramatically amplified (FIG. 7). More than 10 cycle shifts at the crossing point of the amplification curve for all primer sets were observed when a constant amount of heat-solubilized agarose gel was used as the PCR template. These observations indicate that the genomic amplification occurring within the agarose gel comprised substantial numbers of cycles of template DNA replication, most likely a multiple displacement amplification reaction primed by randomly hybridized hexamer oligonucleotides and carried out by the Phi29 DNA polymerase.

Quantitative Assessment of the Enzymatic Amplification in Agarose Gel

By using the real-time QPCR data, the amplification yield at each locus from various amounts of input DNA was calculated in accordance with the following formula:

Yield=target locus DNA content in 4 microliters post-amplification solution×total volume of post-amplification solution/4 microliters The target locus DNA content relative to the original amount of nonamplified identical human genomic DNA was calculated by the standard curve method.

Figure 8:
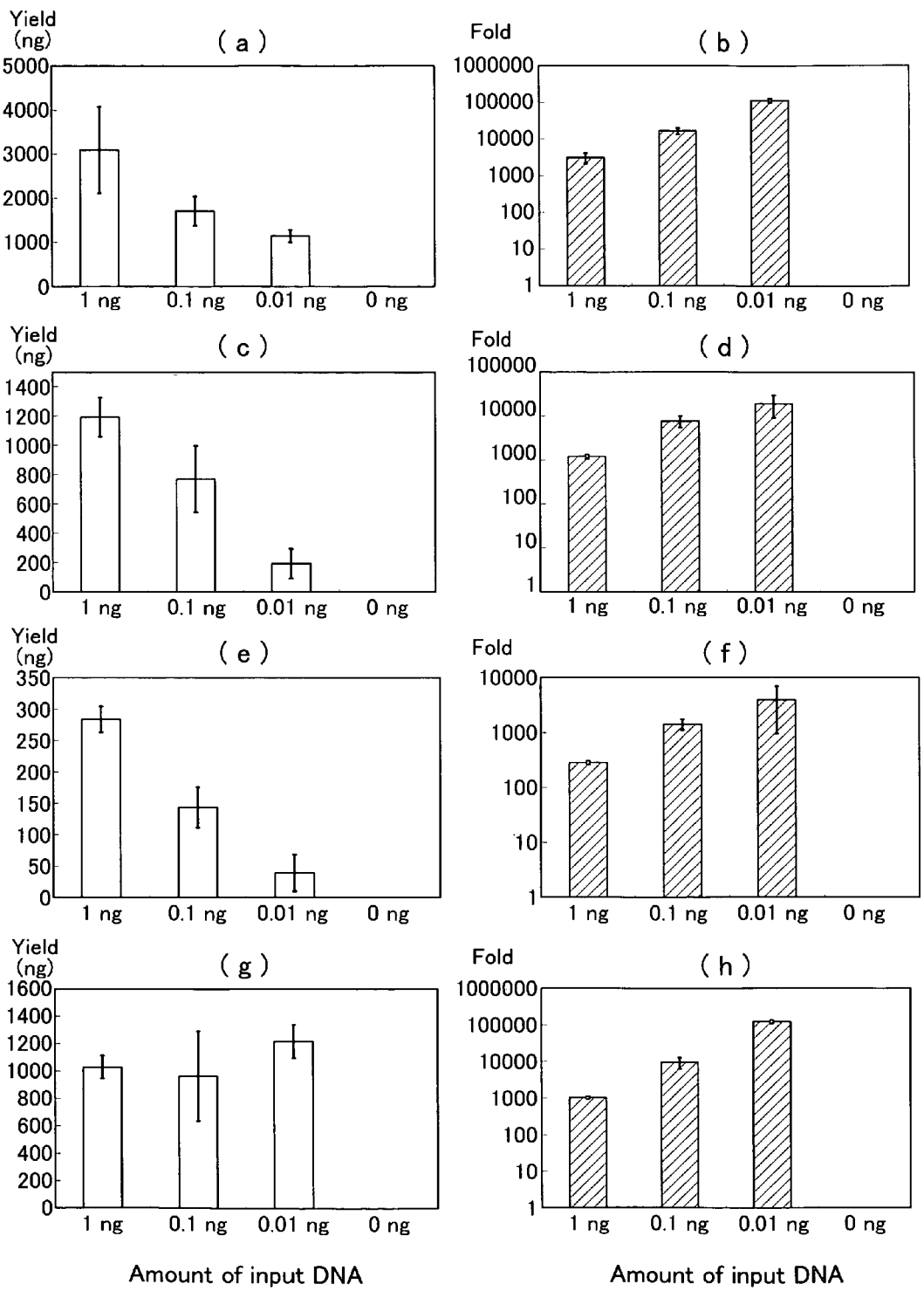
FIG. 8: Yield and fold amplification of human genomic DNA. Agarose gels immobilized with 1, 0.1, 0.01, or 0 ng of human genomic DNA were incubated with Phi29 DNA polymerase for 16 h. Yield and fold amplification of each locus (a, b: chromosome 5; c, d: chromosome 11; e, f chromosome 17; and g, h: mitochondrial DNA) within each gel are plotted.

The calculation results are shown in FIGS. 8*a, c, e*, and *g*. Nuclear chromosome loci showed yields proportional to the amount of input DNA, though the yield range varied among loci, whereas the yield of the mitochondrial DNA locus was relatively constant regardless of the amount of input DNA. These differences might reflect different amplification kinetics between linear and circular template DNA immobilized within the limited space of an agarose gel.

Next, the fold amplification of each locus was calculated in accordance with the following formula:

Fold amplification=amplification yield of the target locus/amount of input DNA

The calculation results are shown in FIGS. 8*b, d, f*, and *h*. Fold amplification was found to be inversely related to the amount of input DNA. Decreasing the amount of input DNA led to a clear increase in the fold amplification up to 120 000-fold, with circular mitochondrial DNA showing a steeper trend. These observations indicate that the crowdedness of the template DNA immobilized within agarose gel acted as a rate-limiting factor, especially for circular DNA. Presumably, individual template DNAs were placed in distinct matrices of the gel and their amplification became physically impaired as the matrices became occupied by the amplification products. Thus, the higher level of crowding of the template DNA caused earlier saturation of the reaction. Amplification of circular DNA might need more space than that of linear DNA.

It will be obvious to those having skill in the art that many changes may be made in the above-described details of the preferred embodiments of the present invention. The scope of the present invention, therefore, should be determined by the following claims.

TABLE 1

Oligonucleotide sequences

| Chr | Gene | SNP | Type | Sequence | Product size | SEQ ID NO |
|---|---|---|---|---|---|---|
| First screening ||||||||
| 5 | Securin | | PCR.F | 5'-ACGTTGGATGGCTGCTGTTTGATCTACCTG | 90 bp | SEQ ID NO:1 |
| | | | PCR.R | 5'-ACGTTGGATGGGGAAACAACCAATGTTGGG | | SEQ ID NO:2 |
| 11 | ATM | rs664677 | PCR.F | 5'-ACGTTGGATGGCAAGGTGAGTATGTTGG | 108 bp | SEQ ID NO:3 |
| | | | PCR.R | 5'-ACGTTGGATGCACTCAGAAAACTCACTG | | SEQ ID NO:4 |
| | | | Opext1* | 5'-(C6-amino)TGATAAAAGCACTCAGAAAACTCACTGAAAGGTTATTA-(LNA) | | SEQ ID NO:5 |
| | | | Opext2† | 5'-(C6-amino)ATAAAAGCACTCAGAAAACTCACTGAAAGGTTATTG-(LNA) | | SEQ ID NO:6 |
| 17 | LIGIII | | PCR.F | 5'-ACGTTGGATGTTTTTATCCCCTGCACCCTG | 94 bp | SEQ ID NO:7 |
| | | | PCR.R | 5'-ACGTTGGATGTAGGATTTGGGGTTTGGGTC | | SEQ ID NO:8 |
| mtDNA | | | PCR.F | 5'-CACAGCCACTTTCCACACAG | 243 bp | SEQ ID NO:9 |
| | | | PCR.R | 5'-GGGGTTGTATTGATGAGATTAGTAG | | SEQ ID NO:10 |
| Second screening ||||||||
| 11 | ACAT1 | rs2280332 | PCR.F | 5'-ACGTTGGATGTCAGTTTCTACCTCCCTTCC | 109 bp | SEQ ID NO:11 |
| | | | PCR.R | 5'-ACGTTGGATGACCTCAACATTCAGGGTTGG | | SEQ ID NO:12 |
| | | | Opext1 | 5'-(C6-amino)TATGCTGCTATAGTAATTCAGAGCCCAAACT(LNA) | | SEQ ID NO:13 |
| | | | Opext2 | 5'-(C6-amino)CTGCTATAGTAATTCAGAGCCCAAACG(LNA) | | SEQ ID NO:14 |
| 11 | NPAT | rs228589 | PCR.F | 5'-ACGTTGGATGCTTGTTCCTTATTGTGGTTCCTGCT | 211 bp | SEQ ID NO:15 |
| | | | PCR.R | 5'-ACGTTGGATGATCACCGCCAGTCTCAACTCGTAA | | SEQ ID NO:16 |
| | | | Opext1 | 5'-(C6-amino)CCGGGTCCAATAACCCTCCT(LNA) | | SEQ ID NO:17 |
| | | | Opext2 | 5'-(C6-amino)CCGGGTCCAATAACCCTCCA(LNA) | | SEQ ID NO:18 |
| 11 | ATM | rs1800054 | PCR.F | 5'-ACGTTGGATGCTGATTCGAGATCCTGAAAC | 100 bp | SEQ ID NO:19 |
| | | | PCR.R | 5'-ACGTTGGATGATACCTAAAAACAGCATCCC | | SEQ ID NO:20 |
| | | | Opext1 | 5'-(C6-amino)TGAAACAATTAAACATCTAGATCGGCATTCAGATTC-(LNA) | | SEQ ID NO:21 |
| | | | Opext2 | 5'-(C6-amino)TGAAACAATTAAACATCTAGATCGGCATTCAGATTG-(LNA) | | SEQ ID NO:22 |
| 11 | ATM | rs1800057 | PCR.F | 5'-ACGTTGGATGCACAGTTCTTTTCCCGTAGG | 117 bp | SEQ ID NO:23 |
| | | | PCR.R | 5'-ACGTTGGATGTGGTGATGATTGTCAGCAAG | | SEQ ID NO:24 |
| | | | Opext1 | 5'-(C6-amino)AGTTCTTTTCCCGTAGGCTGATCC(LNA) | | SEQ ID NO:25 |
| | | | Opext2 | 5'-(C6-amino)AGTTCTTTTCCCGTAGGCTGATCG(LNA) | | SEQ ID NO:26 |
| 11 | ATM | rs1801516 | PCR.F | 5'-ACGTTGGATGGTCAGACTGTACTTCCATAC | 87 bp | SEQ ID NO:27 |
| | | | PCR.R | 5'-ACGTTGGATGCCTGAACATGTGTAGAAAGC | | SEQ ID NO:28 |
| | | | Opext1 | 5'-(C6-amino)-ACTGTACTTCCATACTTGATTCATGATATTTTACTCCAAA(LNA) | | SEQ ID NO:29 |
| | | | Opext2 | 5'-(C6-amino)TGTACTTCCATACTTGATTCATGATATTTTACTCCAAG-(LNA) | | SEQ ID NO:30 |
| 11 | C11orf65 | rs227055 | PCR.F | 5'-ACGTTGGATGTTTGTACTTGTTTGCCGGCC | 69 bp | SEQ ID NO:31 |
| | | | PCR.R | 5'-ACGTTGGATGGAAATCCTGCTCTGCCTTTC | | SEQ ID NO:32 |
| | | | Opext1 | 5'-(C6-amino)TTTGCCGGCCCTTAGCTTGAATCA(LNA) | | SEQ ID NO:33 |
| | | | Opext2 | 5'-(C6-amino)CCGGCCCTTAGCTTGAATCG(LNA) | | SEQ ID NO:34 |

\*. Allele 1-distinguishing oligonucleotide. 5'-end is C6-aminoacylated and there is a Locked Nucleic Acid (LNA) at the 3'-end
†. Allele 2-distinguishing oligonucleotide. 5'-end is C6-aminoacylated and there is a LNA at the 3'-end

TABLE 2

Summary of ATM locus screening of EBV-transformed human lymphoblastoid cell lines

| Patient ID | Concentration (cells/gel) | Number of gels | Screening 1* | Screening 2† | % intact‡ |
|---|---|---|---|---|---|
| 1 | 0.05 | 93 | 7 | 3 | 42.9 |
| 2 | 0.05 | 93 | 24 | 16 | 66.7 |
| 3 | 0.05 | 93 | 13 | 5 | 38.5 |
| 4 | 0.05 | 93 | 11 | 6 | 54.5 |
| 5 | 0.05 | 93 | 18 | 6 | 33.3 |
| 6 | 0.05 | 93 | 22 | 5 | 22.7 |
| 7 | 0.10 | 93 | 30 | 5 | 16.7 |
| 8 | 0.10 | 93 | 23 | 8 | 34.8 |
| 9 | 0.10 | 93 | 17 | 6 | 35.3 |
| 10 | 0.10 | 93 | 22 | 8 | 36.4 |
| Average | | | 18.7 | 6.8 | 38.2 |
| SD | | | 6.9 | 3.6 | 14.3 |

*Number of gels positive for the chromosome 11 (rs664677 SNP) amplicon
†Number of gels positive for amplicons of the entire ATM locus
‡Proportion of positives from screen 2 among screen 1 positives

What is claimed is:

1. A method for amplifying genomic DNA comprising the steps of:
   (1) incubating a cell-containing agarose solution at a pH of 9 to 12 and a temperature of 45° to 80° C. and producing a genomic DNA-dispersed agarose solution thereby forming a dispersion of 0.002 to 1 copies/5 microliter of spatially separated single-stranded genomic DNA, then
   (2) solidifying the genomic DNA-dispersed agarose solution to produce a genomic DNA-dispersed agarose gel and neutralizing the pH of the gel; and then
   (3) adding a DNA polymerase with strand displacement activity, primer and dNTP to the genomic DNA-dispersed agarose gel and incubating the gel at a temperature of 0 to 60° C. to amplify the genomic DNA.

2. The method according to claim 1, wherein the genomic DNA to be amplified is human genomic DNA.

3. The method according to claim 1, wherein the genomic DNA to be amplified is nuclear DNA.

4. The method according to claim 1, wherein the incubation of the step (1) is carried out at a 20 pH of 11 and a temperature of 60° C.

5. The method according to claim 1, wherein 0.2 to 0.4 copies/5 microliter of single-stranded genomic DNA is dispersed in the genomic DNA-dispersed agarose solution of the step (1).

6. The method according to claim 1, wherein the solidification of the step (2) is carried out at a temperature of 0 to 10° C.

7. The method according to claim 1, wherein the neutralized gel of the step (2) has a pH of 7.5.

8. The method according to claim 1, wherein the DNA polymerase in the step (3) has an optimum temperature of 30° C.

9. The method according to claim 1, wherein the DNA polymerase of the step (3) is Phi29 DNA polymerase.

10. The method according to claim 1, wherein the DNA polymerase of the step (3) is Phi29 DNA polymerase and the primer of the step (3) consists of the following sequence:
   $N_1N_2N_3N_4N_5N_6$ ($N_1$, $N_2$, $N_3$, $N_4$, $N_5$ and $N_6$ each may be identical or different, which are bases randomly selected from the group consisting of A, C, G, and T, with $N_5$ and $N_6$ being modified with phosphorothioate).

11. The method according to claim 1, wherein the incubation of the step (3) is carried out at a temperature of 30° C.

* * * * *

SEQUENCE LISTING

<160> NUMBER OF SEQ ID NOS: 34

<210> SEQ ID NO 1
<211> LENGTH: 30
<212> TYPE: DNA
<213> ORGANISM: Artificial
<220> FEATURE:
<223> OTHER INFORMATION: Forward primer for Securin

<400> SEQUENCE: 1
acgttggatg gctgctgttt gatctacctg                                    30

<210> SEQ ID NO 2
<211> LENGTH: 30
<212> TYPE: DNA
<213> ORGANISM: Artificial
<220> FEATURE:
<223> OTHER INFORMATION: Reverse primer for Securin

<400> SEQUENCE: 2
acgttggatg gggaaacaac caatgttggg                                    30

<210> SEQ ID NO 3
<211> LENGTH: 28
<212> TYPE: DNA
<213> ORGANISM: Artificial
<220> FEATURE:
<223> OTHER INFORMATION: Forward primer for ATM rs664677

<400> SEQUENCE: 3
acgttggatg gcaaggtgag tatgttgg                                      28

<210> SEQ ID NO 4
<211> LENGTH: 28
<212> TYPE: DNA
<213> ORGANISM: Artificial
<220> FEATURE:
<223> OTHER INFORMATION: Reverse primer for ATM rs664677

<400> SEQUENCE: 4
acgttggatg cactcagaaa actcactg                                      28

<210> SEQ ID NO 5
<211> LENGTH: 38
<212> TYPE: DNA
<213> ORGANISM: Artificial
<220> FEATURE:
<223> OTHER INFORMATION: ATM rs664677 allele 1-distinguishing oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (38)..(38)
<223> OTHER INFORMATION: 3'-end is an Locked Nucleic Acid(LNA).

<400> SEQUENCE: 5
tgataaaagc actcagaaaa ctcactgaaa ggttatta                               38

<210> SEQ ID NO 6
<211> LENGTH: 36
<212> TYPE: DNA
<213> ORGANISM: Artificial
<220> FEATURE:
<223> OTHER INFORMATION: ATM rs664677 allele 2-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (36)..(36)
<223> OTHER INFORMATION: 3'-end is an Locked Nucleic Acid(LNA).

<400> SEQUENCE: 6
ataaaagcac tcagaaaact cactgaaagg ttattg                                 36

<210> SEQ ID NO 7
<211> LENGTH: 30
<212> TYPE: DNA
<213> ORGANISM: Artificial
<220> FEATURE:
<223> OTHER INFORMATION: Forward primer for LIGIII

<400> SEQUENCE: 7
acgttggatg tttttatccc ctgcaccctg                                        30

<210> SEQ ID NO 8
<211> LENGTH: 30
<212> TYPE: DNA
<213> ORGANISM: Artificial
<220> FEATURE:
<223> OTHER INFORMATION: Reverse primer for LIGIII

<400> SEQUENCE: 8
acgttggatg taggatttgg ggtttgggtc                                        30

<210> SEQ ID NO 9
<211> LENGTH: 20
<212> TYPE: DNA
<213> ORGANISM: Artificial
<220> FEATURE:
<223> OTHER INFORMATION: Forward primer for mtDNA

<400> SEQUENCE: 9
cacagccact ttccacacag                                                   20

<210> SEQ ID NO 10
<211> LENGTH: 25
<212> TYPE: DNA
<213> ORGANISM: Artificial
<220> FEATURE:
<223> OTHER INFORMATION: Reverse primer for mtDNA

```
<400> SEQUENCE: 10
ggggttgtat tgatgagatt agtag                                         25

<210> SEQ ID NO 11
<211> LENGTH: 30
<212> TYPE: DNA
<213> ORGANISM: Artificial
<220> FEATURE:
<223> OTHER INFORMATION: Forward primer for ACAT1 rs2280332

<400> SEQUENCE: 11
acgttggatg tcagtttcta cctcccttcc                                    30

<210> SEQ ID NO 12
<211> LENGTH: 30
<212> TYPE: DNA
<213> ORGANISM: Artificial
<220> FEATURE:
<223> OTHER INFORMATION: Reverse primer for ACAT1 rs2280332

<400> SEQUENCE: 12
acgttggatg acctcaacat tcagggttgg                                    30

<210> SEQ ID NO 13
<211> LENGTH: 31
<212> TYPE: DNA
<213> ORGANISM: Artificial
<220> FEATURE:
<223> OTHER INFORMATION: ACAT1 rs2280332 allele 1-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (31)..(31)
<223> OTHER INFORMATION: 3'-end is an Locked Nucleic Acid(LNA).

<400> SEQUENCE: 13
tatgctgcta tagtaattca gagcccaaac t                                  31

<210> SEQ ID NO 14
<211> LENGTH: 27
<212> TYPE: DNA
<213> ORGANISM: Artificial
<220> FEATURE:
<223> OTHER INFORMATION: ACAT1 rs2280332 allele 2-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (27)..(27)
<223> OTHER INFORMATION: 3'-end is an Locked Nucleic Acid(LNA).

<400> SEQUENCE: 14
ctgctatagt aattcagagc ccaaacg                                       27

<210> SEQ ID NO 15
<211> LENGTH: 35
<212> TYPE: DNA
<213> ORGANISM: Artificial
<220> FEATURE:
<223> OTHER INFORMATION: Forward primer for NPAT rs228589

<400> SEQUENCE: 15
```
acgttggatg cttgttcctt attgtggttc ctgct                    35

<210> SEQ ID NO 16
<211> LENGTH: 34
<212> TYPE: DNA
<213> ORGANISM: Artificial
<220> FEATURE:
<223> OTHER INFORMATION: Reverse primer for NPAT rs228589

<400> SEQUENCE: 16
acgttggatg atcaccgcca gtctcaactc gtaa                     34

<210> SEQ ID NO 17
<211> LENGTH: 20
<212> TYPE: DNA
<213> ORGANISM: Artificial
<220> FEATURE:
<223> OTHER INFORMATION: NPAT rs228589 allele 1-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (20)..(20)
<223> OTHER INFORMATION: 3'-end is an Locked Nucleic Acid(LNA).

<400> SEQUENCE: 17
ccgggtccaa taaccctcct                                     20

<210> SEQ ID NO 18
<211> LENGTH: 20
<212> TYPE: DNA
<213> ORGANISM: Artificial
<220> FEATURE:
<223> OTHER INFORMATION: NPAT rs228589 allele 2-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (20)..(20)
<223> OTHER INFORMATION: 3'-end is an Locked Nucleic Acid(LNA).

<400> SEQUENCE: 18
ccgggtccaa taaccctcca                                     20

<210> SEQ ID NO 19
<211> LENGTH: 30
<212> TYPE: DNA
<213> ORGANISM: Artificial
<220> FEATURE:
<223> OTHER INFORMATION: Forward primer for ATM rs1800054

<400> SEQUENCE: 19
acgttggatg ctgattcgag atcctgaaac                          30

<210> SEQ ID NO 20
<211> LENGTH: 30
<212> TYPE: DNA
<213> ORGANISM: Artificial
<220> FEATURE:
<223> OTHER INFORMATION: Reverse primer for ATM rs1800054

<400> SEQUENCE: 20
acgttggatg atacctaaaa acagcatccc                                    30

<210> SEQ ID NO 21
<211> LENGTH: 36
<212> TYPE: DNA
<213> ORGANISM: Artificial
<220> FEATURE:
<223> OTHER INFORMATION: ATM rs1800054 allele 1-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (36)..(36)
<223> OTHER INFORMATION: 3'-end is an Locked Nucleic Acid(LNA).

<400> SEQUENCE: 21
tgaaacaatt aaacatctag atcggcattc agattc                             36

<210> SEQ ID NO 22
<211> LENGTH: 36
<212> TYPE: DNA
<213> ORGANISM: Artificial
<220> FEATURE:
<223> OTHER INFORMATION: ATM rs1800054 allele 2-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (36)..(36)
<223> OTHER INFORMATION: 3'-end is an Locked Nucleic Acid(LNA).

<400> SEQUENCE: 22
tgaaacaatt aaacatctag atcggcattc agattg                             36

<210> SEQ ID NO 23
<211> LENGTH: 30
<212> TYPE: DNA
<213> ORGANISM: Artificial
<220> FEATURE:
<223> OTHER INFORMATION: Forward primer for ATM rs1800057

<400> SEQUENCE: 23
acgttggatg cacagttctt ttcccgtagg                                    30

<210> SEQ ID NO 24
<211> LENGTH: 30
<212> TYPE: DNA
<213> ORGANISM: Artificial
<220> FEATURE:
<223> OTHER INFORMATION: Reverse primer for ATM rs1800057

<400> SEQUENCE: 24
acgttggatg tggtgatgat tgtcagcaag                                    30

<210> SEQ ID NO 25
<211> LENGTH: 24
<212> TYPE: DNA
<213> ORGANISM: Artificial
<220> FEATURE:
<223> OTHER INFORMATION: ATM rs1800057 allele 1-distinguishing
      oligonucleotide
<220> FEATURE:
<221> NAME/KEY: misc_feature
<222> LOCATION: (1)..(1)

```
<223> OTHER INFORMATION: 5'-end is C6-aminoacylated.
<220> FEATURE:
<221> NAME/KEY: misc_feature
<222> LOCATION: (24)..(24)
<223> OTHER INFORMATION: 3'-end is an Locked Nucleic Acid(LNA).

<400> SEQUENCE: 25
agttcttttc ccgtaggctg atcc                                          24

<210> SEQ ID NO 26
<211> LENGTH: 24
<212> TYPE: DNA
<213> ORGANISM: Artificial
<220> FEATURE:
<223> OTHER INFORMATION: ATM rs1800057 allele 2-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (24)..(24)
<223> OTHER INFORMATION: 3'-end is an Locked Nucleic Acid(LNA).

<400> SEQUENCE: 26
agttcttttc ccgtaggctg atcg                                          24

<210> SEQ ID NO 27
<211> LENGTH: 30
<212> TYPE: DNA
<213> ORGANISM: Artificial
<220> FEATURE:
<223> OTHER INFORMATION: Forward primer for ATM rs1801516

<400> SEQUENCE: 27
acgttggatg gtcagactgt acttccatac                                    30

<210> SEQ ID NO 28
<211> LENGTH: 30
<212> TYPE: DNA
<213> ORGANISM: Artificial
<220> FEATURE:
<223> OTHER INFORMATION: Reverse primer for ATM rs1801516

<400> SEQUENCE: 28
acgttggatg cctgaacatg tgtagaaagc                                    30

<210> SEQ ID NO 29
<211> LENGTH: 40
<212> TYPE: DNA
<213> ORGANISM: Artificial
<220> FEATURE:
<223> OTHER INFORMATION: ATM rs1801516 allele 1-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (40)..(40)
<223> OTHER INFORMATION: 3'-end is an Locked Nucleic Acid(LNA).

<400> SEQUENCE: 29
actgtacttc catacttgat tcatgatatt ttactccaaa                         40

<210> SEQ ID NO 30
<211> LENGTH: 38
```

```
<212> TYPE: DNA
<213> ORGANISM: Artificial
<220> FEATURE:
<223> OTHER INFORMATION: ATM rs1801516 allele 2-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (38)..(38)
<223> OTHER INFORMATION: 3'-end is an Locked Nucleic Acid(LNA).

<400> SEQUENCE: 30
tgtacttcca tacttgattc atgatatttt actccaag                              38

<210> SEQ ID NO 31
<211> LENGTH: 30
<212> TYPE: DNA
<213> ORGANISM: Artificial
<220> FEATURE:
<223> OTHER INFORMATION: Forward primer for C11orf65 rs227055

<400> SEQUENCE: 31
acgttggatg tttgtacttg tttgccggcc                                       30

<210> SEQ ID NO 32
<211> LENGTH: 30
<212> TYPE: DNA
<213> ORGANISM: Artificial
<220> FEATURE:
<223> OTHER INFORMATION: Reverse primer for C11orf65 rs227055

<400> SEQUENCE: 32
acgttggatg gaaatcctgc tctgcctttc                                       30

<210> SEQ ID NO 33
<211> LENGTH: 24
<212> TYPE: DNA
<213> ORGANISM: Artificial
<220> FEATURE:
<223> OTHER INFORMATION: C11orf65 rs227055 allele 1-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (24)..(24)
<223> OTHER INFORMATION: 3'-end is an Locked Nucleic Acid(LNA).

<400> SEQUENCE: 33
tttgccggcc cttagcttga atca                                             24

<210> SEQ ID NO 34
<211> LENGTH: 20
<212> TYPE: DNA
<213> ORGANISM: Artificial
<220> FEATURE:
<223> OTHER INFORMATION: C11orf65 rs227055 allele 2-distinguishing
      oligonucleotide
<220> FEATURE:
<221> NAME/KEY: misc_feature
<222> LOCATION: (1)..(1)
<223> OTHER INFORMATION: 5'-end is C6-aminoacylated.
<220> FEATURE:
<221> NAME/KEY: misc_feature
<222> LOCATION: (20)..(20)
<223> OTHER INFORMATION: 3'-end is an Locked Nucleic Acid(LNA).
```

```
<400> SEQUENCE: 34 ccggcccta gcttgaatcg                                            20
```